US005573913A

United States Patent [19]

Rosemeyer et al.

[11] Patent Number: 5,573,913
[45] Date of Patent: Nov. 12, 1996

[54] 3'-RNA LABELLING WITH TERMINAL TRANSFERASE

[75] Inventors: Viola Rosemeyer, Riedvochel; Rudolf Seibl, Penzberg; Andreas Laubrock, Kiel, all of Germany

[73] Assignee: Boehringer Mannheim GmbH, Mannheim, Germany

[21] Appl. No.: 396,148

[22] Filed: Feb. 28, 1995

[30] Foreign Application Priority Data

Feb. 28, 1994 [DE] Germany .......................... 44 06 524.8

[51] Int. Cl.$^6$ .............................. C12Q 1/68; C12Q 1/70; C12P 19/34; C07H 21/04
[52] U.S. Cl. .................................. 435/6; 435/5; 435/91.1; 435/91.2; 536/24.3; 536/24.31; 536/24.32
[58] Field of Search .................................. 435/6, 5, 91.2, 435/91.1; 536/24.3–24.33; 535/174

[56] References Cited

U.S. PATENT DOCUMENTS 4,591,564   5/1986   Watson ...................... 435/194

FOREIGN PATENT DOCUMENTS

4119076A1   12/1992   Germany .

OTHER PUBLICATIONS

*Boehringer Mannheim Biochemia*, Catalog; "Biochemicals for Molecular Biology" and Boehringer Mannhiem; Colloquium Molecular Biology.

*Feds Letters*, vol. 18, No. 2, Nov. 1, 1971, pp. 280–282, "Oligoribonucleotides as primer for terminal deoxynucleotidyl transferase".

*Biochem. and Biophys. Res. Communications*, vol. 46, III, "Enzymatic synthesis of polynucleotides covalently linked to an oligoribonucleotide primer". pp. 2141–2147, 1972.

*Anal. Biochem.* (1991), vol. 192, No. 1, Jan. 1991, "Non-radioactive labeling of oligonucleotides in vitro with the hapten digoxigenin by tailing with terminal transferase". pp. 222–231.

*Anal. Biochem.* (1995), vol. 224, No. 1, Jan. 1995, "Non-radioactive 3'-end-labeling of RNA molecules of different lengths by terminal deoxynucleotidyltransferase". pp. 446–449.

Duck et al, BioTechniques 9(2) 142–145, 1990.

Guitierrez et al, The Lancet, 339:715–721, 1992.

James, W. Antiviral Chemistry and Chemotheraphy 2(4)199–214, 1991.

Primary Examiner—W. Gary Jones
Assistant Examiner—Dianne Rees
Attorney, Agent, or Firm—Nikaido, Marmelstein, Murray & Oram LLP

[57] ABSTRACT

The present invention concerns a process for introducing non-radioactively labelled deoxynucleotides into nucleic acids and RNA molecules which at their 3' end contain at least one deoxynucleotide which carries a non-radioactive marker group.

43 Claims, 7 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:1:

CGCCGCGUCG CAGAAGAUCU CAAUC    2 5

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTGAGATCTT CTGCGACGCG G    2 1

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (xi) SEQUENCE DESCRIPTION: SEQ ID NO:3:

TTGAGATCTT ATGCGACGCG G                        21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTGAGATCTC ACGCGACGCG G                        21

3'-RNA LABELLING WITH TERMINAL TRANSFERASE

DESCRIPTION

The present invention concerns a process for introducing non-radioactively labelled deoxynucleotides into nucleic acids and RNA molecules which contain at least one deoxynucleotide at their 3' end which carries a non-radioactive marker group.

Labelled RNA molecules are often used as hybridization probes since RNA-DNA hybrids are more stable than DNA-DNA hybrids (Srivastava, R. A. K. and Schonfeld, G. (1991) BioTechniques 11, 584–587). A well-known method for the production of non-radioactively labelled RNA probes is in vitro transcription using labelled nucleotides as a substrate for RNA polymerases (Langer, P. R., Waldrop, A. A. and Ward, D. C. (1981), Proc. Natl. Acad. Sci. USA 78, 6633–6637; Höltke, H.-J. and Kessler, C. (1990) Nucleic Acids Res. 18, 5843–5851). In an in vitro transcription it is possible to label RNA at its 5' end using biotinylated dinucleotides as initiator oligonucleotides (Pitulle, C., Kleineidam, R. G., Sproat, B. and Krupp, G. (1992) Gene 112, 101–105).

In contrast RNA molecules that are already present can only be provided with an enzymatic 5'-end label by using polynucleotide kinase and [$\gamma^{32}$P]-ATP, i.e. radioactively (Richardson, C. C. (1981) In Boyer, P. D. (ed.) The Enzymes, Academic Press, New York, Vol. XIV, pp. 299–314).

A chemical 3'-end-labelling of RNA molecules using biotin is described by von Broker et al. (Nucleic Acids Res. 5 (1978), 363–384) and Sodja and Davidson (Nucleic Acids Res. 5 (1978), 385–401). In this process biotin is bound to the 3'-terminal ribose sugar of RNA in a multistep reaction via a $NH_2(CH_5)NH_2$ spacer or via cytochrome C. This reaction comprises the oxidation of the sugar with periodate, reaction of the resulting dialdehyde with a $NH_2$ group of the spacer or of cytochrome C with formation of a Schiff base, a subsequent reduction with $BH_4^-$ and covalent coupling of biotin to the spacer or to cytochrome C. This labelling method is a tedious and time-consuming process which has not been used in practice.

A radioactive enzymatic 3'-end-labelling of RNA has been demonstrated with poly(A) polymerase and T4 RNA ligase. Poly(A) polymerase is used to attach [$\alpha^{32}$P]-ATP to the 3' end of RNA molecules (Winter, G. and Brownlee, G. G. (1978) Nucleic Acids Res. 5, 3129–3139). T4 RNA ligase is used to attach [5'-$^{32}$P]-pCp to the 3' end of RNA molecules (Uhlenbeck, O. C. and Gumport, R. I. (1982) In Boyer, P. D. (ed.) The Enzymes, Academic Press, New York, Vol. XV, p. 31–58). T4 RNA ligase can also be used to non-radioactively label RNA with biotin, tetramethylrhodamine and fluorescein derivatives of $P^1$-(6-aminohex-1-yl)-$P^2$-(5'-adenosine)pyrophosphate (Richardson, R. W. and Gumport, R. I. (1983) Nucleic Acids Res. 11, 6167–6184).

The attachment of nucleotides to the 3' end of RNA molecules using RNA ligase and poly(A) polymerase does, however, have considerable problems. In the case of RNA ligase there are basically two possibilities of 3'-labelling the RNA by using different types of substrates, i.e. labelling with a single nucleotide or labelling by ligation with a 3'-labelled oligonucleotide. When labelling with a single nucleotide, this nucleotide must have a phosphate at the 3' and 5' position i.e. it must be present in the pNp form. The attachment of such a nucleotide which carries a non-radioactive marker group to a RNA molecule with the aid of T4 RNA ligase is not known. Non-radioactive marker groups can therefore only be transferred directly with a spacer onto the 3'-hydroxyl end of RNA using T4 RNA ligase (cf. Richardson and Gumport, supra). The attachment of nucleotides with a marker group bound to the nucleotide base to the 3' end of RNA molecules is not known.

Moreover when using a single nucleotide as the substrate it is not possible to vary the number of attached nucleotides and thus the intensity of the labelling since only a single substrate molecule can be attached per reaction cycle. When using a 3'-labelled oligonucleotide as the substrate for T4 RNA ligase, an additional sequence is also attached which could for example interfere with hybridization experiments. Moreover long incubation periods of for example ca. 12 hours are necessary for efficient attachment of substrate molecules to RNA by T4 RNA ligase which can lead to a significant degradation of the very hydrolysis-sensitive RNA.

The efficient labelling of 3' ends of RNA molecules with poly(A) polymerase is limited to the use of ATP and ATP derivatives since bases other than A are accepted much more poorly by the enzyme. Oligonucleotides have an extremely low efficiency as acceptor molecules. The attachment of oligoribonucleotides to the 3' end of RNA molecules by poly(A) polymerase is not known. It is not possible to attach non-radioactively labelled nucleotides.

In a publication by Roychoudhury and Kössel (Eur. J. Biochem. 22 (1971), 310–320) it is described that an oligodeoxynucleotide with two ribonucleotide units at the 3' end can serve as a nucleic acid acceptor molecule for the attachment of dATP molecules by terminal deoxynucleotidyl transferase. However, even at very high ATP concentrations, the reaction rate is substantially reduced by the presence of the two ribonucleotides at the 3' end of the nucleic acid acceptor molecule.

In a publication by Feix (FEBS Letters 18 (1971), 280–282) it is described that the oligoribonucleotide $A_6$ can serve as a nucleic acid acceptor molecule for the attachment of dCTP to the 3' end by terminal deoxynucleotidyl transferase. However, it was found that dCTP is incorporated into the ribonucleic acid acceptor molecule with an extremely low efficiency compared with a deoxyribonucleic acid acceptor molecule. In a later publication the same author (Feix, Biochem. Biophys. Res. Comm. 46 (1972), 2141–2147) writes that a ribonucleic acid acceptor molecule exhibits a negligible activity as a primer for the attachment of deoxynucleotides by terminal deoxynucleotidyl transferase.

Therefore no process is known from the state of the art with which RNA molecules that are already present can be provided in a simple manner with one or several non-radioactive marker groups.

Thus the object of the present invention was to provide a process for introducing non-radioactive marker groups into RNA molecules in which the disadvantages and difficulties of the state of the art are at least partially eliminated. In particular the object of the present invention was to provide a process which enables an efficient, rapid introduction of different nucleotides which carry non-radioactive marker groups into RNA molecules.

This object is achieved by a process for introducing nucleotides which carry a non-radioactive marker group into nucleic acids, which is characterized in that at least one non-radioactively labelled deoxynucleotide is attached by terminal deoxynucleotidyl transferase (EC 2.7.7.31) to the 3' end of a nucleic acid acceptor molecule with at least one 3'-terminal ribonucleotide.

Surprisingly the process according to the invention enables non-radioactive marker groups to be attached by a simple enzymatic reaction within a short time period to the 3' end of a nucleic acid acceptor molecule with a 3' terminal ribonucleotide. The reaction proceeds efficiently and it is possible to introduce several marker groups, which if desired, may also be different, into the nucleic acid acceptor molecule within a single reaction cycle. A further advantage of the process is that the reagents, i.e. the terminal deoxynucleotidyl transferase as well as the deoxynucleotides with a non-radioactive marker group, are commercially available substances.

Terminal deoxynucleotidyl transferase (also denoted nucleoside triphosphate: DNA deoxynucleotidylexo-transferase or TdT) is an enzyme which occurs in the bone marrow and thymus of mammals (see e.g. Kung, P. C., Gottlieb, P. D. and Baltimore, D., J. Biol. Chem. 251 (1976), 2399–2404; Ratcliff, R. L., The Enzymes 14a (1981), 105–118) and is obtainable for example from Boehringer Mannheim GmbH, Mannheim, Germany with a specific activity of ca. 60,000 U/mg. TdT isolated from mammalian tissue (in particular calf thymus) as well as TdT produced by recombinant DNA techniques is suitable for the process according to the invention.

The use of terminal deoxynucleotidyl transferase (TdT) to attach one or several deoxynucleotides to the 3' end of single-stranded or double-stranded DNA and to label oligodeoxyribonucleotides with biotin-modified or digoxigenin-modified nucleotides is known (see e.g. Deng, G. R. and Wu, R. (1983) Methods Enzymol. 100, 96–116; Hayes, F. N., Mitchell, V. E., Ratcliff, R. L., Schwartz, A. W. and Williams, D. L. (1966) Biochemistry 5, 3625–3629; Roychoudhury, R., Jay, E. and Wu, R. (1976) Nucleic Acids Res. 3, 863–877; Kumar, A., Tchen, P., Roullet, F. and Cohen, J. (1988) Anal. Biochem. 169, 376–382; Riley, L. K., Marshall, M. E. and Coleman, M. S. (1986) DNA 5, 333–337; Schmitz, G. G., Walter, T., Seibl, R. and Kessler, C. (1991) Anal. Biochem. 192, 222–231). However, deoxynucleotides with a non-radioactive marker group are accepted much more poorly by the TdT than unlabelled or radioactively labelled deoxynucleotides.

It was therefore extremely surprising that deoxynucleotides which carry a non-radioactive marker group are accepted at all as substrates for TdT when using a nucleic acid acceptor molecule with at least one 3'-terminal ribonucleotide.

The nucleic acid acceptor molecule or the primer in the process according to the invention is a nucleic acid to which the substrate molecules, i.e. in general deoxyribonucleotide triphosphates, are attached with cleavage of pyrophosphate and formation of a phosphodiester bond. This nucleic acid has at least one ribose sugar at its 3' end with a free 3' hydroxyl group and can be any desired chemically or/and enzymatically synthesized nucleic acid, e.g. a nucleic acid produced in vivo by a cell, which, apart from the 3'-terminal ribonucleotide, can contain any nucleotide units i.e. in particular deoxyribonucleotide or/and ribonucleotide units. However, nucleic acid acceptor molecules are preferred which have at least two and in particular at least three ribose sugars at their 3' end. Nucleic acid molecules are particularly preferred which are composed of more than 50% and essentially exclusively of ribonucleotide units i.e. RNA molecules and particularly those which have been produced in vivo.

The minimum length of the nucleic acid acceptor molecule for the process according to the invention is 3 nucleotides, preferably 8 nucleotides and particularly preferably 12 nucleotides. The maximum length of the nucleic acid acceptor molecule is actually arbitrary i.e. nucleic acids with a length of several thousand, e.g. 2000 to 3000 bases can be used without difficulty. In addition it is preferred that the nucleic acid acceptor molecule in the process according to the invention is present in the form of a single-stranded molecule and has no stable, pronounced secondary structures (e.g. hair-pin structures) at its 3' end. mRNA molecules can also for example be used as nucleic acid acceptor molecules for the process according to the invention.

In the process according to the invention, deoxynucleotides and namely particularly 2'-deoxynucleoside triphosphates or/and 2',3'-deoxynucleoside triphosphates are attached as substrates to a nucleic acid. When 2'-deoxynucleoside triphosphates are used as substrates, the 3' end of the acceptor nucleic acid can be extended by several nucleotides, whereas the attachment of a 2',3'-deoxynucleoside triphosphate leads to a 3'-H-end and thus to a chain termination.

The nucleotide bases in the non-radioactively labelled deoxynucleotides can be the natural bases adenine, guanine, cytosine, thymine, uracil as well as base analogues such as inosine, pseudouracil, fluorouracil and the like. Specific examples of deoxynucleotides are for instance biotin-dUTP and digoxigenin-dUTP.

In the process according to the invention, it is possible to use on the one hand non-radioactively labelled deoxynucleotides alone or combinations of unlabelled (or e.g. radioactively labelled) deoxynucleotides and non-radioactively labelled deoxynucleotides as substrates. The use of combinations of unlabelled and labelled deoxyribonucleotides is preferred if it is intended to introduce several marker groups into the acceptor nucleic acid.

The process according to the invention also provides a novel and effective method for the enzymatic introduction of marker groups into various types of RNA molecules by attaching preferably non-radioactively labelled deoxynucleotides to the 3' end of the RNA molecules. A population of in vivo-generated RNA molecules, e.g. mRNA molecules, which have been isolated from a cell are preferably used as RNA molecules. Preferred examples of nucleotides which carry a non-radioactive marker group are nucleotides which carry a fluorescent, chemiluminescent or NMR active marker group or/and a marker group capable of high affinity binding to a reaction partner. Marker groups are particularly preferred which are capable of high affinity binding to a reaction partner e.g. biotin or biotin derivatives which are able to bind to avidin or streptavidin or haptens which are able to bind to a specific antibody. Digoxigenin-modified or biotin-modified nucleotides are particularly preferred. However, it is also possible to use other non-radioactively labelled deoxynucleotides such as deoxynucleotides modified for example with fluorescein, rhodamine, coumarin, other fluorophores or other haptens. Further examples of suitable marker groups may be found in "Non-radioactive Labeling and Detection of Biomolecules", C. Kessler ed., Springer Verlag 1992, in particular p. 6; p. 28).

TdT can be used to attach a single modified 2',3'-dideoxynucleotide to the 3' end of a nucleic acid acceptor molecule. On the other hand it is also possible to attach several deoxynucleotides to such RNA molecules using one or several different modified 2'-deoxynucleoside triphosphates e.g. digoxigenin-dUTP or biotin-dUTP. The attachment of a large number of deoxynucleotides can for example be achieved with a mixture of unlabelled and labelled 2'-deoxynucleotide triphosphates e.g. digoxigenin-dUTP and dATP.

Using suitable reaction conditions the process according to the invention enables several labels to be introduced into a single nucleic acid acceptor molecule in a single reaction cycle during the 3'-end-labelling of nucleic acid acceptor molecules with deoxynucleotides which carry a non-radioactive marker group. Preferably up to 20 labels are attached which enables the labelled nucleic acid to be detected with a very high sensitivity. 2 to 10 marker groups are preferably introduced. The marker groups can be the same or different. Preferably a total of up to 200 (unlabelled and labelled) deoxynucleotides are attached per reaction cycle, particularly preferably 1 to 50 deoxynucleotides per reaction cycle.

The concentration of the nucleic acid acceptor molecule in the reaction mixture is preferably 0.1 µmol/l to 20 µmol/l, particularly preferably 0.5 µmol/l to 10 µmol/l. The concentration of the deoxynucleotides is preferably 0.1 to 2.0 mmol/l in the reaction mixture. If it is intended to attach a single nucleotide to the 3' end of the acceptor nucleic acid, a 2',3' dideoxynucleotide is used as the substrate, the attachment of which leads to a chain termination. In order to attach a low number of nucleotides, one or several labelled 2'-deoxynucleotides are used as a substrate. In order to attach a larger number (e.g. >10) of nucleotides, a mixture of one or several unlabelled 2'-deoxynucleotides and one or several labelled 2'-deoxynucleotides can be used as the substrate in which case the molar ratio of unlabelled to labelled substrate molecules is preferably in the range of 2:1 to 20:1 particularly preferably 5:1 to 15:1.

A particular advantage of the process according to the invention compared to known RNA end-labelling processes is that the reaction can be carried out within a short period of preferably 10 minutes to 2 hours, particularly preferably of 20 minutes to 1 hour, most preferably ca. 30 minutes. In addition it is preferred that the reaction is carried out in the presence of a RNase inhibitor, e.g. RNAsin, since commercial TdT preparations can contain a certain residual RNase activity.

On the other hand it is preferable to use an essentially RNase-free TdT. The removal of residual RNase activity from TdT preparations can be carried out in a well-known manner (see e.g. Sambrook et al., Molecular Cloning. A Laboratory Manual, 2nd edition (1989), Cold Spring Harbor Laboratory Press, USA, p. B17–B19) by affinity chromatography on Agarose-5'-(4-aminophenylphosphoryl)uridine-2'-(3')phosphate, by adsorption to macaloid or by heating in the presence of iodoacetate. A TdT is particularly preferred for carrying out the process according to the invention which in a function test, e.g. when 4 µg MS2-RNA is incubated for 4 hours at 37° C. in 50 µl test buffer containing TdT, shows no measurable change of the RNA bands at a concentration of up to 50 U/ml, preferably of up to 500 U/ml TdT.

In addition it is preferred to carry out the reaction at a pH value of 6.0 to 7.5 and at a concentration of divalent metal ions, in particular $Zn^{2+}$, $Co^{2+}$, $Mg^{2+}$ or $Mn^{2+}$, of 2 to 10 mmol/l.

Particularly preferred conditions for a reaction mixture are 20–200 pmol nucleic acid acceptor molecule, 5–50 U TdT (1 U TdT is the enzyme activity which causes the incorporation of 1 nmol dAMP into acid-insoluble products within 60 minutes at 37° C. using $(dT)_6$ as the nucleic acid acceptor), 100–300 mmol/l potassium cacodylate, 5–50 mmol/l Tris/HCl pH 6.6, 0.05–0.5 mg/ml bovine serum albumin, 2–10 mmol/l $CoCl_2$ and 0.1–2.0 mmol/l deoxynucleotide in a final volume of 10–200 µl. The reaction is carried out for about 30 minutes at 37° C. The attachment of a single nucleotide to the 3' end can for example be accomplished by using 0.5 mmol/l of a 2',3'-deoxynucleotide, e.g. digoxigenin-11-ddUTP or biotin-16-ddUTP. In order to attach a small number of nucleotides (e.g. up to 5), 0.5 mmol/l of a labelled 2'-deoxynucleotide, e.g. digoxigenin-11-dUTP or biotin-16-dUTP or a combination of digoxigenin-11-dUTP and digoxigenin-11-ddUTP (0.25 mmol/l in each case) can be used. In order to attach a larger number of nucleotides (e.g. >10), one can for example use a mixture which contains 0.45 mmol/l of a non-labelled 2'-deoxynucleotide such as dATP and 0.05 mmol/l of a labelled 2'-deoxynucleotide e.g. digoxigenin-11-dUTP. In addition it is preferable to add ca. 40 U RNase inhibitor to the mixture or to use TdT without measurable RNase activity. The reaction can be stopped by addition of EDTA.

In a further preferred embodiment of the present invention an already labelled nucleic acid acceptor molecule can be used as the starting material, e.g. a 5'-end-labelled acceptor molecule. A label can be introduced at the 5' end of a ribonucleic acid by polynucleotide kinase and [$\gamma^{32}P$]-ATP in the case of a radioactive label or, in the case of a non-radioactive label, by chemical synthesis, e.g. using an appropriately modified phosphoramidite e.g. a biotinamidite (Applied Biosystems) or by incorporation of an Aminolink II (Applied Biosystems) and subsequent coupling with the label (G. H. Keller and M. H. Manak, DNA Probes, Stockton Press. 1989, page 136 fl.). In this manner it is possible to produce RNA molecules which carry a label at their 5' end as well as at their 3' end. The production of molecules with two different non-radioactive labels at the 5' and 3' end is particularly preferred e.g. RNA molecules with a biotin residue at the 5' end and one or several digoxigenin residues at the 3' end or vica versa.

A further particular advantage of the process according to the invention is that, in contrast for instance to poly(A) polymerase, terminal deoxynucleotidyl-transferase accepts all nucleotides (e.g. dATP, dGTP, dCTP, dTTP, dUTP, dITP) and the corresponding 2',3'-dideoxy analogues as substrates.

A further subject matter of the present invention is a RNA molecule which contains in the region of its 3' end at least one deoxynucleotide which carries a non-radioactive marker group and the label is covalently bound to the nucleotide base of the deoxynucleotide. Such molecules cannot be produced by using known enzymatic RNA labelling methods e.g. by labelling with poly(A) polymerase or T4 RNA ligase. In the method described by Richardson and Gumport, supra, of non-radioactive labelling of RNA with RNA ligase, an ADP is used on the β phosphorus atom of which an aminohexyl residue is bound with the non-radioactive label. The RNA ligase transfers this aminohexyl residue onto the 3' hydroxyl end of a RNA with release of AMP. As a result the label is bound terminally to a phosphate residue via the aminohexyl spacer. In contrast the label attached by the process according to the invention is bound covalently to the nucleotide base of the attached nucleotide. The advantage of the process according to the invention is that the 3' end of the RNA is still available—either for ligation of a second sequence or for the attachment of further nucleotides by the terminal transferase i.e. it is possible to introduce several marker groups which leads to an increase in the sensitivity. The RNA molecule according to the invention preferably carries at least two non-radioactive marker groups, most preferably 2 to 10 marker groups.

The non-radioactively labelled deoxynucleotide in the RNA molecule according to the invention is preferably a digoxigenin-labelled or a biotin-labelled deoxynucleotide. Furthermore it is preferred that the RNA molecule additionally carries a label in the region of its 5' end.

The present invention in addition concerns the use of the products of the process according to the invention within the field of molecular biological research and pharmaceuticals e.g as a probe for the detection of nucleic acid analytes, as a template for the production of cDNA molecules, in the isolation and purification of nucleic acids, in the sequencing of RNA molecules and for the production of antisense nucleic acids.

A preferred application is the detection of a nucleic acid analyte with a defined target sequence in a sample liquid. The specificity of the test for nucleic acid molecules is achieved by hybridization with a nucleic acid sequence complementary to the target sequence. The direct or indirect identification of such hybrids thus infers the presence of the target sequence. A problem in these test methods is the frequently small amount of target DNA. In order to nevertheless obtain a clear signal above the background, various amplification techniques can be applied: amplification of the target sequence, amplification of the signal or a combination of both types of amplification.

One possibility of signal amplification is the "cycling probe" method described by P. Duck et al. in BioTechniques 9 (1990), 142–147 which comprises the steps:

(a) Contacting a sample liquid with labelled RNA molecules complementary to a section of a DNA analyte under conditions which allow hybridization with the labelled RNA molecules when the analyte is present, (b) treating the sample liquid with RNase H under such conditions that a degradation of the RNA molecules in the hybrid and a release of the degraded RNA fragments occurs when a RNA-DNA hybrid is present (c) if necessary repeating steps (a) and (b) once or several times and (d) detecting the presence or absence of the DNA analytes by determining the degraded RNA fragments or/and the non-degraded RNA molecules.

This cycling probe method is shown schematically in FIG. 6:

RNA molecules complementary to a particular section of the target sequence form RNA-DNA hybrids with the DNA to be detected. The action of RNase H only degrades the RNA portion in each of these hybrids and the fragments diffuse away from the target sequence due to the lower melting temperature. By this means the DNA is available for a further hybridization and degradation cycle. If the RNA molecules are in a molar excess over the target DNA, these two repeatable steps lead to an amplification cycle. If no DNA target sequence was present, then no RNA-DNA hybrids can form and the RNA molecules are not degraded by RNase H.

Thus either the degradation products of the RNA molecules or the decrease in the amount of RNA molecules originally used can be detected. Detection of the degradation products of the previously labelled RNA molecules usually involves gel electrophoretic techniques. In this case the presence of target DNA in the cycling probe mixture is inferred from an increased rate of migration of the labelled RNA degradation products or from a decrease in the intensity of the band which represents the intact RNA.

The use of RNA molecules according to the invention with two different non-radioactive labels which can be separated from one another represents a further development of this system. The first of the two labels which is preferably located in the region of the 5' end of the RNA molecule can be used to bind the RNA to a solid phase and the analyte can be detected by determining the second label which is preferably located in the region of the 3' end of the RNA molecule. On the other hand, the first label can of course also be located in the region of the 3' end and the second label in the region of the 5' end of the RNA molecules. In this connection it should be noted that the labels in this case do not have to be limited to the extreme ends (i.e. the 5' or 3' position). For example in the case of a RNA molecule the second or/and third nucleotide at the 5' end as well as several nucleotides at the 3' end can be labelled.

The analyte is now detected either by determining the signal decrease of the second label on the solid phase or/and by the increase in the signal of the second label in the liquid phase or on a second solid phase which can bind with high affinity to the second label. Preferred examples of two such separable labels are biotin and digoxigenin or another hapten or two different haptens e.g. digoxigenin and fluorescein. The biotin label can bind to a solid phase coated with streptavidin and the hapten label can bind to a solid phase coated with anti<hapten>antibody. The procedure for the individual reaction steps is shown in FIG. 7:

In this procedure no time-consuming gel electrophoretic techniques are on the one hand, necessary and, on the other hand, it is possible to avoid the use of radioactive substances. The principle of this process is based on the fact that in the presence of a target DNA the RNase H leads to a separation of the two labels after the hybridization by degradation of the RNA molecules. If one of these two labels is now bound to a suitable surface, then, when the separation is completed, the decrease in the number of the other labels on the solid phase or/and their increase in the supernatant can be detected. If the DNA target sequence is absent, both labels remain linked together and thus coupled to an appropriate surface so that no RNA degradation products can be detected. The choice of detection reactions that can be analyzed photometrically and of microtitre plates (MTP) as a test format enables quantitative results as well as a high sample throughput.

An advantage of using the process according to the invention for the detection of nucleic acids is also that a subsequent labelling of in vivo-generated RNA is possible e.g. with a biotin label, so that the RNA molecules labelled in this manner can be used as probes to detect nucleic acid analytes. The RNAs according to the invention can, in addition to their use in the cycling probe method, also be used as probes in other nucleic acid detection methods e.g. in a direct hybridization or in a sandwich hybridization.

A further application of the RNA molecules according to the invention is the isolation of specific DNA sequences. Thus probes according to the invention can be produced to "fish out" specific nucleic acids in which case the probes can for example be bound by means of a biotin label to a streptavidin-coated solid phase and degraded for example by alkaline degradation after hybridization with the "fished" DNA sequence. By this means the "fished" DNA is in solution and is available for further experiments.

A further possibility of using the RNA according to the invention is to isolate and purify RNA. Thus by attaching a non-radioactively modified nucleotide to the 3' end of isolated RNA molecules, these can be purified by binding to a suitable solid phase (e.g. streptavidin coating, anti-digoxigenin antibody coating). By attaching a series of the same nucleotides (e.g. a G or C tail), the RNA itself can be specifically purified by means of this tail without introduced marker groups. In addition a G or C tail enables a cDNA synthesis with a corresponding complementary primer and this construct is more stable than previously used constructs with a poly(A) tail and oligo(dT) primers.

Isolated RNA with an unknown sequence can therefore be provided with a tail in order to bind a complementary primer for cDNA synthesis and the tail can be examined by incorporating labels and an oligonucleotide complementary to this tail can serve as a primer for cDNA synthesis. In a modification of this method refolding of polyC-polyG tail, that is formed by means of a short tailing period with one nucleotide (e.g. dCTP) and subsequent tailing with an increased concentration of the complementary nucleotide (e.g. dGTP), can be utilized to synthesize a cDNA strand with reversed transcriptase without using an additional primer.

An improved isolation of specific RNA sequences by subtractive or differential hybridization is also possible. Thus the control RNA can be bound to a solid phase, by subsequent modification (e.g. with biotin-labelled or digoxigenin-labelled nucleotides) using TdT the RNA to be examined can be transcribed into a more stable cDNA (reversal of the standard procedure described in the literature) which can hybridize with the bound RNA to locate the differential sequences.

The process according to the invention can also be used to purify RNA-binding proteins. For this the RNA involved in the protein binding is 3'-terminally labelled and then used for binding to proteins, the RNA complexes and thus the proteins can be isolated by subsequent binding to a solid phase.

Yet a further possibility of application is RNA sequencing. The prerequisites for sequencing by base specific cleavage from the 3' end are fulfilled by attaching only one nucleotide to the 3' end of a RNA to be sequenced. In addition the labelled RNA can be immobilized and thus it is possible to carry out a solid phase sequencing according to the chain termination method.

A further application is in the production of a pharmaceutical agent e.g. for the antisense technology in which 3'-modified RNA molecules according to the invention can be used diagnostically and therapeutically.

Finally the present invention also concerns a terminal deoxynucleotidyl transferase which is essentially RNase-free and is used for attaching deoxynucleotides, in particular non-radioactively labelled deoxynucleotides, to RNA molecules.

An essentially RNase-free terminal deoxynucleotidyl transferase can be the component of a reagent kit for attaching deoxynucleotides to the 3' end of RNA molecules. The terminal transferase is preferably present in a volume activity of 10 to 50×$10^3$ U/ml in a 50% glycerol buffer, pH 6.5. Further components of the buffer are preferably a thiol reagent e.g. 2-mercaptoethanol at a concentration of 1 to 10 mmol/l, NaCl at a concentration of 150 to 250 mmol/l, sodium cacodylate at a concentration of 150 to 250 mmol/l and EDTA at a concentration of 0.1 to 2 mmol/l. The terminal transferase is stable in such a buffer system at −20° C.

The invention is elucidated further by the following examples and figures.

EXAMPLES

Example 1

Non-radioactive labelling of RNA molecules

The conditions for attaching a tail of non-radioactively labelled nucleotides to the 3' end of RNA was as follows: 1 μg oligoribonucleotide (TdT 1: 5'-CGCCGCGUCGCA-GAAGAUCUCAAUC-3' corresponding to 121 pmol) [SEQ ID No: 1] was incubated for 30 minutes at 37° C. with 25 U TdT (Boehringer Mannheim) in 200 mmol/l potassium cacodylate, 25 mmol/l Tris/HCl (pH 6.6), 0.25 mg/ml bovine serum albumin, 5 mmol/l $CoCl_2$ and 0.5 mmol/l deoxynucleotide triphosphate (Boehringer Mannheim) in a final volume of 30 μl. The attachment of only one nucleotide to the 3' end of the oligoribonucleotide was carried out using 0.5 mmol/l digoxigenin (DIG)-11-ddUTP or biotin-16-ddUTP. 0.5 mmol/l DIG-11-dUTP or biotin-16-dUTP or a combination of DIG-11-dUTP and DIG-11-ddUTP (0.25 mol/l in each case) was used for short tails. For longer tails a mixture of nucleotides was used which contained 0.45 mmol/l dATP and 0.05 mmol/l DIG-11-dUTP. 40 U RNase inhibitor (Boehringer Mannheim) was added since TdT may also contain a certain residual RNase activity. The reaction was stopped by addition of EDTA. Glycogen was added as a carrier for the subsequent ethanol precipitation.

1 μg MS2-RNA, tRNA from E. coli or a mixture of in vitro transcripts (300–1600 bases, RNA molecular weight marker III) (all from Boehringer Mannheim) were tailed in analogous reactions as described above with TdT and 0.5 mmol/l DIG-dUTP.

Figures 1, 2A:
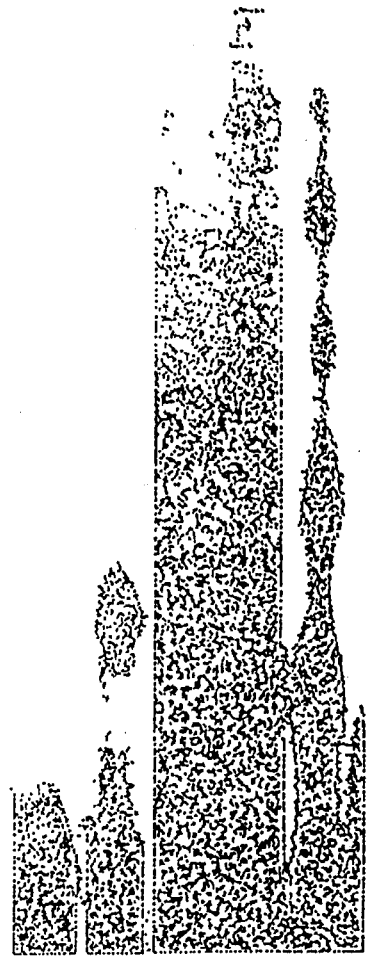
FIG. 1: shows the autoradiogram of a labelling reaction with a synthetic oligoribonucleotide.
FIGS. 2A and 2B: shows the sensitivity of the detection of labelled RNA molecules.

Before the TdT reaction the oligonucleotides were radioactively 5'-terminally labelled with ($\gamma^{32}P$)ATP and polynucleotide kinase for the molecular analysis. After the 3' tailing reaction the products were separated on a 12% polyacrylamide-SM urea sequencing gel and subsequently analyzed autoradiographically. The detection of the incorporation of a non-radioactive label is carried out using anti-DIG-alkaline phosphatase or streptavidin alkaline phosphatase and nitroblue tetrazolium salt and 5-bromo-4-chloro-3-indolyl phosphate in a colorimetric immunoassay described by Schmitz et al. (Anal. Biochem. 192 (1991), 222–231). The result of the tailing reaction of the 5'-($^{32}P$) oligoribonucleotide TdT 1 is shown in FIG. 1. Lane 1 shows the ribonucleotide TdT 1 without a non-radioactive label, lane 2 shows the labelling with DIG-ddUTP, lane 3 shows the labelling with DIG-dUTP for 15 minutes, lane 4 shows the labelling with DIG-dUTP for 30 minutes and lane 5 shows the labelling with biotin-dUTP. Up to 4 DIG-deoxynucleotides could be attached in the tailing reaction using DIG-dUTP. With biotin-dUTP most products contained 1 to 4 modified nucleotides, in some products a fifth nucleotide was also attached. Labelling with biotin-ddUTP (not shown)

or DIG-ddUTP (lane 1) led to attachment of a single nucleotide.

Labelling with a nucleotide mixture of dATP and DIG-dUTP led to tail lengths of up to about 50 nucleotides. The tailing reaction was completed after about a 30 minute incubation and the product pattern remained the same for the next 2 hours.

A further series of experiments is shown in FIG. 2 in which oligonucleotides and polynucleotides labelled at the 3' end with DIG were applied to a membrane in a 1:10 dilution series. FIG. 2a shows the sensitivity of the detection of the labelled oligoribonucleotide TdT 1 after reaction in the presence of TdT with various nucleotide compositions:
1. 0.5 mmol/l DIG-ddUTP,
2. 0.25 mol/l DIG-ddUTP and 0.25 mmol/l DIG-dUTP,
3. 0.5 mmol/l DIG-dUTP,
4. 0.05 mmol/l DIG-dUTP and 0.45 mmol dATP.

Figure 2B:
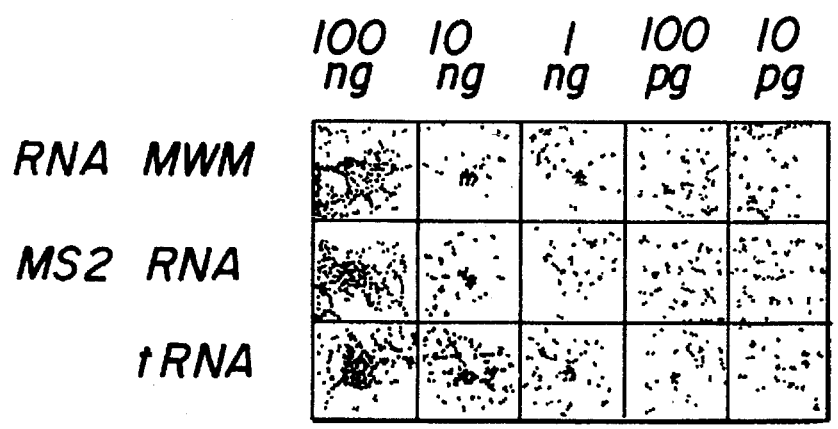

FIG. 2b shows the detection limits for longer RNA molecules which are tailed with 0.5 mmol/l DIG-dUTP (MWM: molecular weight marker, composed of in vitro transcripts).

As can be seen from FIG. 2a, the limit of detection of the labelled oligoribonucleotide TdT 1 with a length of 25 bases depends on the nucleotide or nucleotide mixture used in the tailing reaction. The limit of detection in the case of DIG-ddUTP, which only enables the attachment of a single DIG molecule, was 1 ng. The sensitivity is increased to 100 pg by an equimolar mixture of DIG-ddUTP and DIG-dUTP (0.25 mmol/l in each case) or the addition of DIG-dUTP as the only nucleotide (which enables attachment of up to 4 DIG molecules). The oligoribonucleotide tailed with DIG-dUTP and dATP in a molar ratio of 1:9 shows a sensitivity of 10 pg (1.2 fmol).

It can be seen from FIG. 2b that in vitro-produced RNA transcripts with a length of 300–1600 nucleotides (RNA-MWM), natural tRNA from *E. coli* and viral MS2-RNA can also be tailed with TdT and biotin-dUTP or DIG-dUTP. For this 1 µg of the RNA was in each case incubated with TdT and 0.5 mmol/l DIG-dUTP under the reaction conditions described above. The mixtures were treated with proteinase K in order to exclude false positive signals of complexes between enzyme and labelled nucleotides. Non-incorporated nucleotides were removed by precipitating the reaction products and the latter were then applied to a membrane in dilution series. DIG-dUMP residues attached by TdT were detected as described above. The limits of detection of the RNA molecules tailed with DIG-dUTP as the only nucleotide were determined. It was found that it was possible to detect 100 pg (3.9 fmol) tRNA, 1 ng (3.9 fmol) of in vitro synthesized transcripts and 10 ng (8.5 fmol) MS2-RNA. The differences in the sensitivity may possibly be attributed to the secondary structure of the RNA molecules in particular in the region of the 3' hydroxyl end.

Example 2

1 ng or 10 ng of the RNA oligonucleotide "HBV1" (5' BIO-CGCCGCGUCGCAGAAGAUCUCAAUC-(DIG)$_{1-4}$-3') [SEQ ID No: 1] labelled chemically with 5'-biotin(BIO) and by means of TdT with 3'-DIG was in each case incubated in a volume of 30 µl with different amounts of the DNA oligonucleotides to be detected "DHBV1" (5'-TTGAGATCTTCTGCGACGCGG-3': sequence complementary to HBV1) [SEQ ID No: 2], "MM1DHBV1" (5'-TTGAGATCTTATGCGACGCGG-3': sequence complementary to HBV1 having a central base mismatch) [SEQ ID No. 3] and "MM3DHBV1" (5'-TTGAGATCT-CACGCGACGCGG-3': sequence complementary to HBV1 having three central base mismatches) [SEQ ID No. 4] under the following conditions:

| 1 ng or 10 ng | 5'-BIO-HBV1-DIGtail-3' |
|---|---|
| variable | DNA oligonucleotide to be detected |
| 10 mmol/l | HEPES pH 8.0 |
| 30 mmol/l | NaCl |
| 1 mmol/l | MnCl$_2$ |
| 40 U | RNase inhibitor from placenta (Boehringer Mannheim) |
| 7 µg | bovine serum albumin (BSA) (Boehringer Mannheim, quality for molecular biology) |
| 1 µg | tRNA (Boehringer Mannheim, total tRNA from *E. coli*) |
| 4 U | RNase H (Boehringer Mannheim) |

The mixture was overlayered with 30 µl mineral oil and incubated for 3 hours at 56° C. Subsequently the reaction mixture was made up to a total volume of 210 µl with 180 µl dilution buffer (10 mmol/l HEPES pH 8.0, 30 mmol/l NaCl, 1 mmol/l MnCl$_2$); the 30 µl mineral oil forming the upper phase did not interfere with the further procedure. 100 µl from the lower aqueous phase was pipetted twice into a streptavidin(SA)-coated microtitre plate (MTP) (Boehringer Mannheim) which had been prewashed with washing buffer (PBS, 0.5% (v/v) Tween 20) and the degradation of the RNA oligonucleotide in the presence of the complementary DNA oligonucleotide was detected as follows:

SA-MTP was incubated for 1 hour at 37° C. while shaking (Well-Warm 1, Denley Instruments GmbH Company) in order to enable the biotin coupled to the RNA to bind to streptavidin. After completed attachment the contents of 2 wells in each case (supernatant) were pooled in accordance with the duplicate determinations and used for the detection in a microtitre plate coated with anti-digoxigenin antibodies (<DIG>-MTP) as described below. The SA-MTP was washed five times with 200 µl washing buffer each time. Subsequently 100 µl of a <DIG>-peroxidase(POD)$_{poly}$ conjugate dilution (in conjugate buffer: 100 mmol/l Na phosphate pH 7.5, 0.9% NaCl, 1% Rafulon F4J or BSA fraction V, treated with diethyl pyrocarbonate, sterilized by filtration, stored at +4° C.) was added to each and it was incubated again under the same conditions. Unbound conjugate molecules were removed by washing five times. Then 100 µl substrate solution (2,2'-azino-di-[3-ethylbenzthiazoline sulfonate(6)], ABTS) was added per well; the colour reaction was carried out at 37° C. while shaking. The "optical density" of converted ABTS was measured at 405 nm by means of an ELISA reader (SLT) and the means of the duplicate determinations were calculated after subtracting the blank value (only ABTS). Mixtures that contained no DNA oligonucleotides served as a negative control.

The detection of degraded RNA molecules in the supernatant was carried out in a <DIG>-MTP. Supernatants obtained after incubation in the SA-MTP were used for this: in each case 90 µl was pipetted twice into the <DIG>-MTP prewashed with washing buffer and the subsequent steps for the detection were carried out as described for SA-MTP.

Sensitivity of the detection

Figure 3:
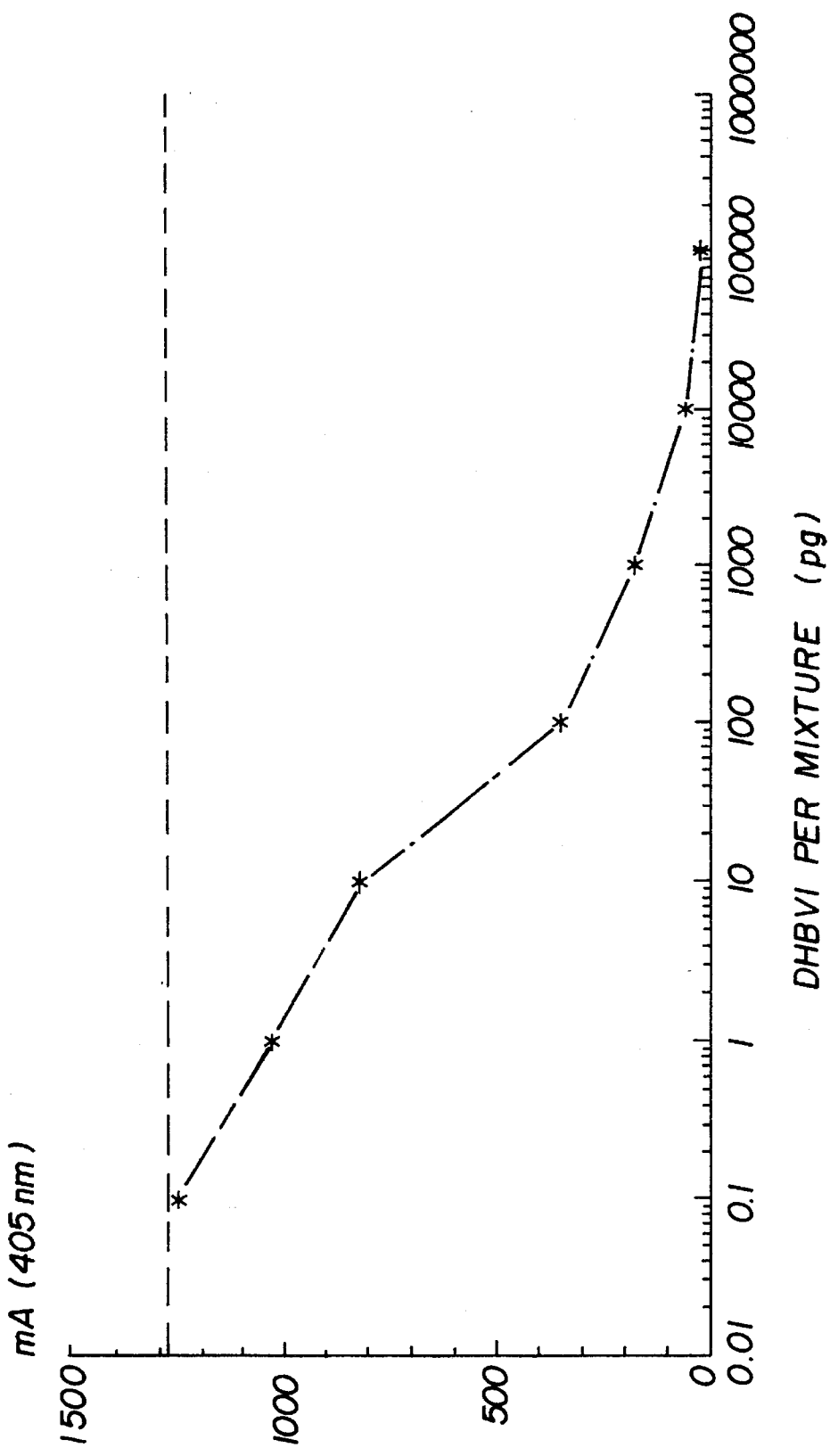
FIG. 3: shows the sensitivity of the detection of a DNA oligonucleotide in a cycling probe reaction.

In each case between 0.1 pg and 100 pg of the DNA oligonucleotide "DHBV1" in a 1:10 dilution series were used in the detection reaction with 1 ng of the RNA oligonucleotide HBV1. Detection in the SA-MTP yielded the values shown graphically in FIG. 3. The relationship between "optical density" (in relative units) and the amount of DNA to be detected (in pg per mixture) is given there. The measured value of the negative control (mixture without "DHBV1") was shown as a horizontal line.

Figure 4:
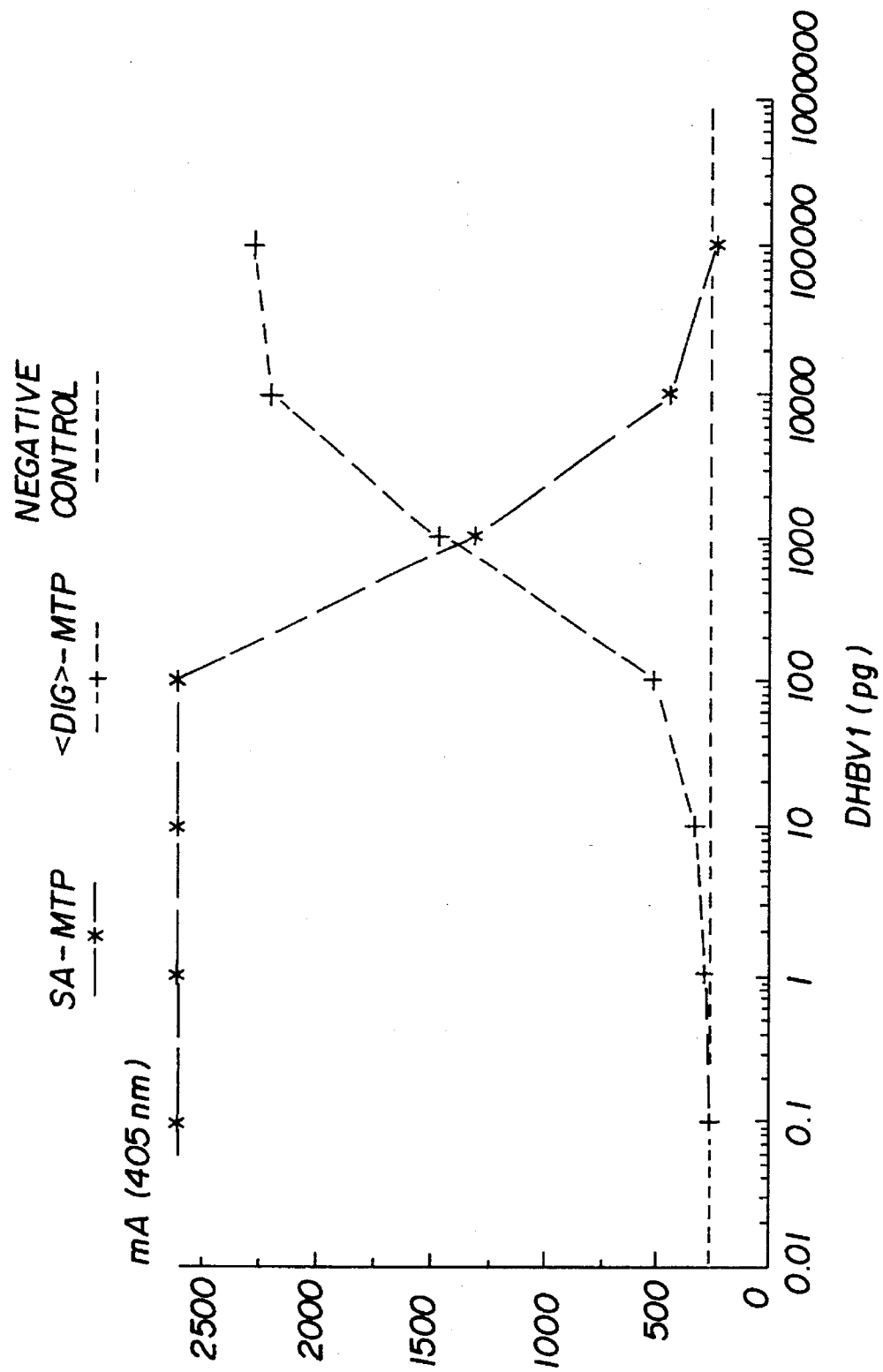
FIG. 4: shows the sensitivity of the detection of a DNA oligonucleotide in a cycling probe reaction with a streptavidin-coated and an anti-digoxigenin-coated microtitre plate

More RNA oligonucleotides were degraded by repeated hybridization and degradation as the amount of target DNA increased. This degradation is reflected by the decrease in the signal obtained. 1 pg (0.121 fmol) of a DNA oligonucleotide can be detected by means of such a mixture. The addition of 10 μg calf thymus DNA per mixture also led to a comparable shape of the curve. The detection in the supernatant in <DIG>-MTP showed an opposite dependency between the signal and amount of DNA: the signal increased with increasing amounts of DNA. Since the obtained values were lower than the values obtained in the SA-MTP, 10 ng 5'-BIO-HBV1-DIG-tail-3' was used in the detection reaction. The dependency of the signal on the amount of DNA is shown graphically in FIG. 4 for the detection in SA-MTP and in <DIG>-MTP. This gives the dependency of the "optical density" (in relative units) on the amount of DNA to be detected (in pg per preparation). The measured value of the negative control (mixture without "DHBV1") for the <DIG>-MTP was shown as a horizontal line; the SA-MTP resulted in values which exceeded the measurable range for the negative control and for mixtures with 0.1 to 100 pg "DHBV1".

Detection in the <DIG>-MTP showed a sensitivity which was about 100-fold less than detection in the SA-MTP.

Specificity of the detection

Figure 5:
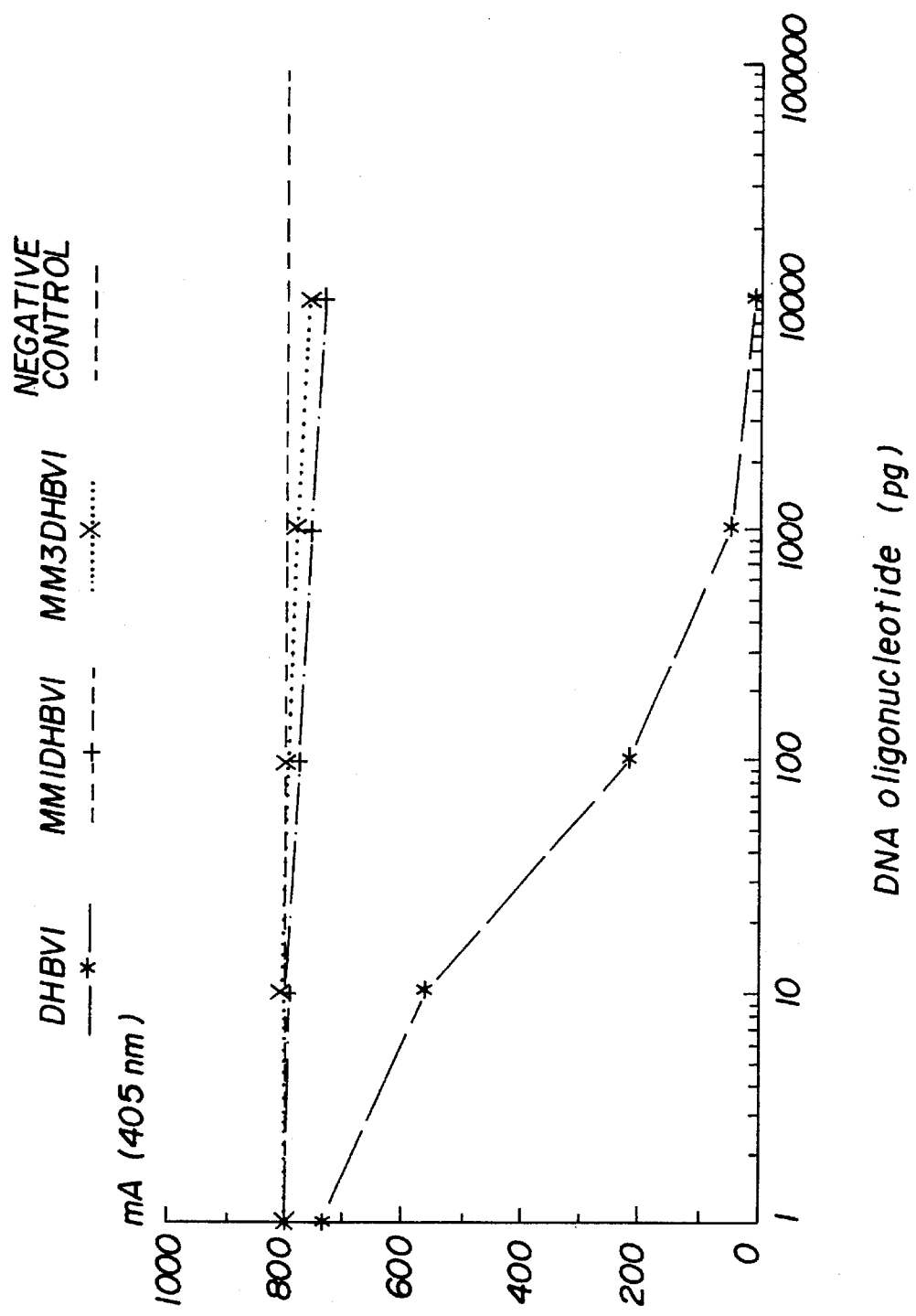
FIG. 5: shows the specificity of the detection of various DNA oligonucleotides.
Figure 6:
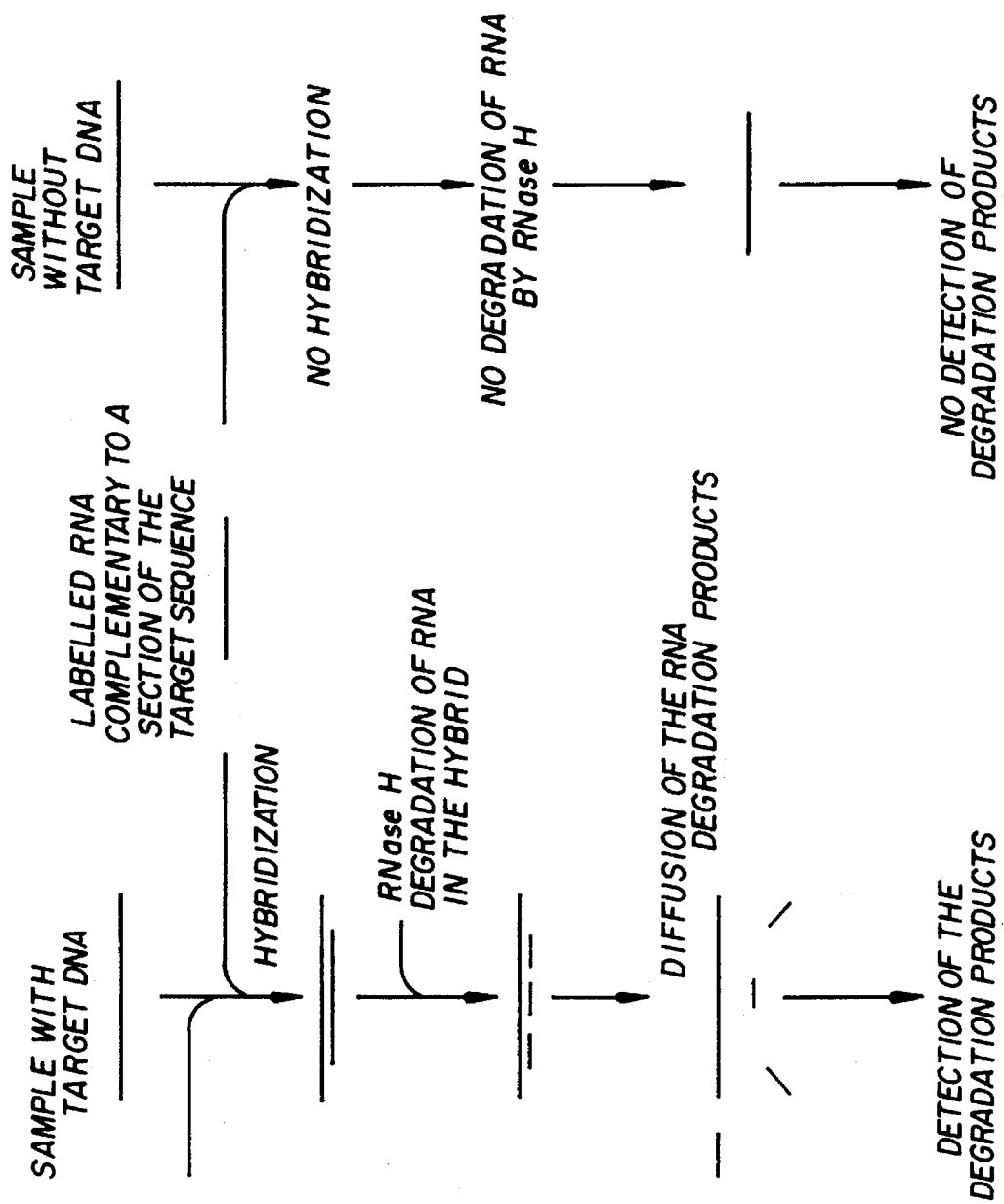
FIG. 6: shows the cycling probe method described in Duck et al.
Figure 7:
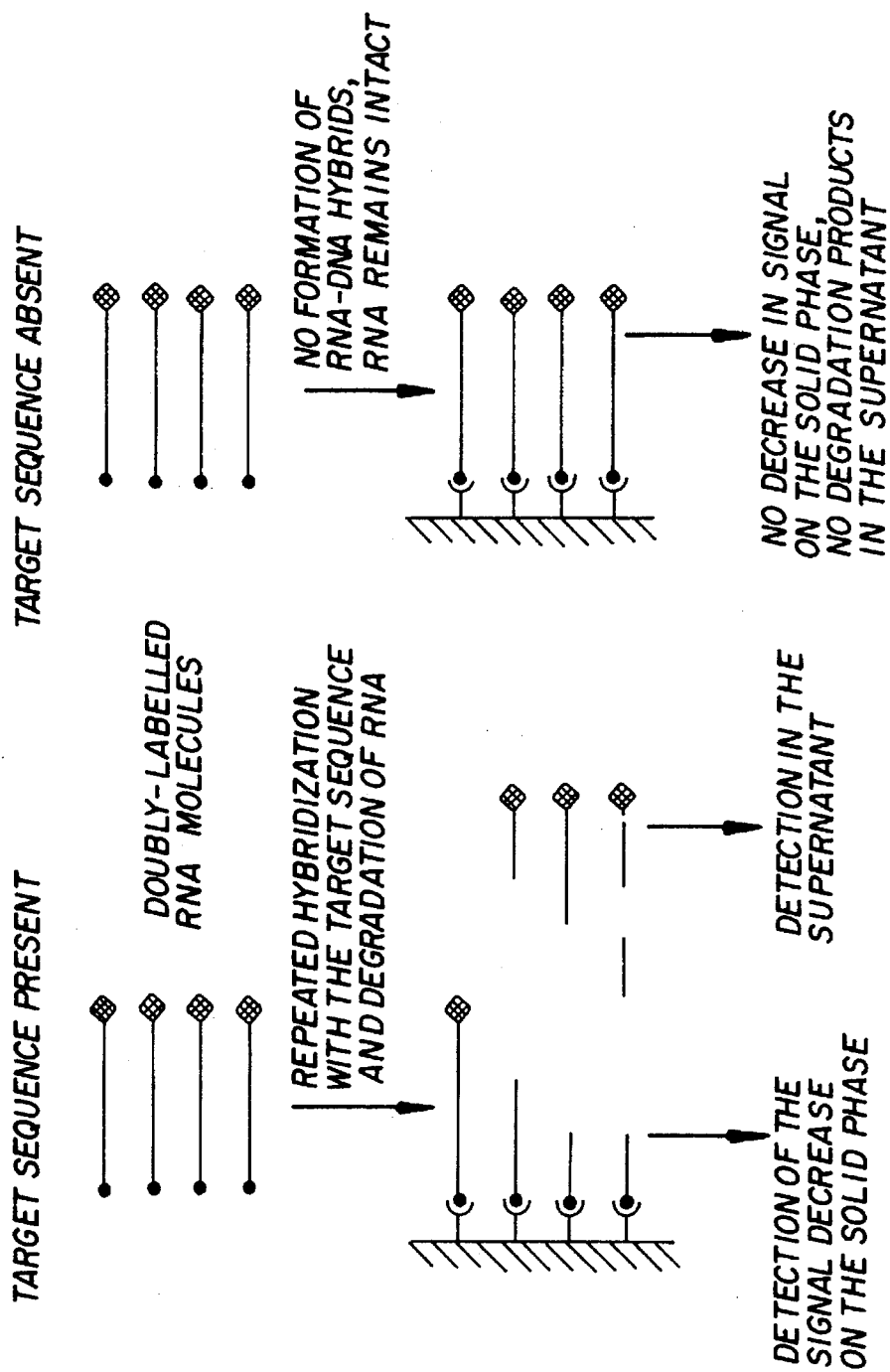
FIG. 7: shows the procedure for the individual reaction steps in accordance with one embodiment of the invention.

The specificity was examined based on three different DNA oligonucleotides which were either perfectly complementary ("DHBV1") to "HBV1" or which had one base mismatch ("MM1DHBV1") or three base mismatches ("MM3DHBV1") at a central position. The corresponding DNA oligonucleotide can only be detected under these reaction conditions when both oligonucleotides are perfectly complementary (FIG. 5). The dependency of "optical density" (in relative units) on the amount of DNA to be detected (in pg per preparation) is given there. The measured value for the negative control (mixture without DNA oligonucleotide) was shown as a horizontal line.

As can be deduced from other experiments, the specificity was based on stringent hybridization conditions. However, these were selected in such a way that the RNase H was still active under such conditions. When the incubation temperature was reduced or the ionic strength in the incubation buffer was increased, it was also possible to detect "MM1DHBV1" and—when the stringency was reduced further- "MM3DHBV1". The sensitivity determined in this manner corresponded to the sensitivity shown in FIG. 3.

We claim:

1. Process for introducing nucleotides which carry a non-radioactive marker group into nucleic acids, wherein
at least one non-radioactively labelled deoxynucleotide is attached by terminal deoxynucleotidyl transferase (EC 2.7.7.31) to the 3' end of a nucleic acid acceptor molecule with at least one 3'-terminal ribonucleotide.

2. Process as claimed in claim 1, wherein
a ribonucleic acid is used as the nucleic acid acceptor molecule.

3. Process as claimed in claim 1, wherein
2'-deoxynucleoside triphosphates or/and 2',3'-dideoxynucleoside triphosphates are used as deoxynucleotides.

4. Process as claimed in claim 1, wherein
deoxynucleotides are used which carry a fluorescent, chemiluminescent or NMR-active marker group or/and a marker group capable of high-affinity binding to a reaction partner.

5. Process as claimed in claim 4, wherein
digoxigenin- or biotin-labelled deoxynucleotides are used.

6. Process as claimed in claim 1, wherein
a nucleic acid acceptor molecule is used which already carries a marker group.

7. Process as claimed in claim 6, wherein
a nucleic acid acceptor molecule labelled in the region of the 5' end is used.

8. Process as claimed in claim 1, wherein
the reaction is carried out in the presence of a RNase inhibitor.

9. Process as claimed in claim 1, wherein the reaction is carried out with a terminal deoxynucleotidyl transferase which shows no measurable RNAse activity at a concentration of up to 50 U/ml terminal deoxynucleotidyl transferase incubated for 4 hours at 37° C.

10. Process as claimed in claim 1, wherein
the reaction is carried out at a pH value of 6.0 to 7.5.

11. Process as claimed in claim 1, wherein
the reaction is carried out at a concentration of a divalent metal ion of 2 to 10 mmol/l.

12. Process as claimed in claim 1, wherein
the reaction is carried out for a period of 10 minutes to 2 hours.

13. Process as claimed in claim 1, wherein
up to 20 non-radioactively labelled deoxynucleotides are attached per reaction cycle.

14. Process as claimed in claim 13, wherein
2 to 10 non-radioactively labelled deoxynucleotides are attached per reaction cycle.

15. Process for introducing marker groups into RNA molecules, wherein
at least one deoxynucleotide which carries a marker group is attached by terminal deoxynucleotidyl transferase (EC 2.7.7.31) to the 3' end of the RNA molecule.

16. Process as claimed in claim 15, wherein
at least one deoxynucleotide is attached which carries a non-radioactive marker group.

17. Process as claimed in claim 15, wherein the RNA molecules are produced in vivo.

18. RNA molecule which, in the region of its 3' end, contains at least one deoxynucleotide which carries a non-radioactive marker group wherein the marker is covalently bound to the nucleotide base of the deoxynucleotide.

19. RNA molecule as claimed in claim 18, wherein
the non-radioactively labelled deoxynucleotide is a digoxigenin- or biotin-labelled deoxynucleotide.

20. RNA molecule as claimed in claim 18, wherein
the RNA molecule carries at least two non-radioactive marker groups in the region of its 3' end.

21. RNA molecule as claimed in claim 19, wherein
the RNA molecule additionally carries a label in the region of its 5' end.

22. Process for detecting a DNA analyte in a cycling probe method, comprising:

(a) contacting a sample liquid with a RNA molecule as claimed in claim 21, wherein the RNA molecule is complementary to a section of the DNA analyte to be detected, to form a hybrid between the RNA molecule and the DNA analyte, (b) treating the sample liquid with RNase H under such conditions that degradation of the RNA molecule in the hybrid occurs, thereby releasing degraded RNA fragments, (c) if necessary, repeating steps (a) and (b) once or several times and (d) detecting the DNA analyte by determining at least one of the degraded RNA fragments and the non-degraded RNA molecule.

23. Process as claimed in claim 22, wherein the RNA molecule carries two different non-radioactive labels that are separable from one another.

24. Process as claimed in claim 23, wherein one of the two different non-radioactive labels is located in the region of the 5' end of the RNA molecule and the other label is located in the region of the 3' end of the RNA molecule.

25. Terminal deoxynucleotidyl transferase which shows no measurable RNAse activity at a concentration of up to 50 U/ml terminal deoxynucleotidyl transferase incubated for 4 hours at 37° C.

26. Reagent kit for attaching deoxynucleotides to the 3' end of RNA molecules, wherein the reagent kit comprises a terminal deoxynucleotidyl transferase as claimed in claim 25.

27. Process for detecting a nucleic acid analyte, comprising hybridizing the RNA molecule as claimed in claim 18 with the nucleic acid analyte to be detected to produce a hybrid, and detecting the hybrid.

28. Process for producing a cDNA molecule, comprising providing the RNA molecule as claimed in claim 18 with a G or C tail, and producing a cDNA molecule, using the RNA molecule as a template.

29. Process for sequencing a RNA molecule, comprising providing the RNA molecule as claimed in claim 18 and sequencing the RNA molecule.

30. Process for detecting a nucleic acid, comprising contacting the RNA molecule as claimed in claim 18 with the nucleic acid to be detected to produce a hybrid, and detecting the hybrid.

31. Process for purifying a nucleic acid, comprising contacting the RNA molecule as claimed in claim 18 with the nucleic acid to be purified to produce a hybrid, detecting the hybrid and thereafter purifying the nucleic acid.

32. RNA molecule produced by attaching at least one non-radioactively labelled deoxynucleotide by terminal deoxynucleotidyl transferase to the 3' end of an acceptor RNA molecule, wherein the RNA molecule, in the region of its 3' end, contains at least one deoxynucleotide which carries a non-radioactive marker group wherein the non-radioactive marker group is covalently bound to the nucleotide base of the deoxynucleotide.

33. RNA molecule as claimed in claim 32, wherein the non-radioactively labelled deoxynucleotide is a digoxigenin- or biotin-labelled deoxynucleotide.

34. RNA molecule as claimed in claim 32, wherein the RNA molecule carries at least two non-radioactive marker groups in the region of its 3' end.

35. RNA molecule as claimed in claim 33, wherein the RNA molecule additionally carries a label in the region of its 5' end.

36. Process for detecting a DNA analyte in a cycling probe method, comprising:

(a) contacting a sample liquid with a RNA molecule as claimed in claim 35, wherein the RNA molecule is complementary to a section of the DNA analyte to be detected, to form a hybrid between the RNA molecule and the DNA analyte, (b) treating the sample liquid with RNAse H under such conditions that degradation of the RNA molecule in the hybrid occurs, thereby releasing degraded RNA fragments, (c) if necessary, repeating steps (a) and (b) once or several times and (d) detecting the DNA analyte by determining at least one of the degraded RNA fragments and the non-degraded RNA molecule.

37. Process as claimed in claim 36, wherein the RNA molecule arrives two different non-radioactive labels that are separable from one another.

38. Process as claimed in claim 37, wherein one of the two different non-radioactive labels is located in the region of the 5' end of the RNA molecule and the other label is located in the region of the 3' end of the RNA molecule.

39. Process for detecting a nucleic acid analyte, comprising hybridizing the RNA molecule as claimed in claim 32 with the nucleic acid analyte to be detected to produce a hybrid, and detecting the hybrid.

40. Process for producing a cDNA molecule, comprising providing the RNA molecule as claimed in claim 32 with a G or C tail, and producing a cDNA molecule, using the RNA molecule as a template.

41. Process for detecting a nucleic acid, comprising contacting the RNA molecule as claimed in claim 32 with the nucleic acid to be detected to produce a hybrid, and detecting the hybrid.

42. Process for purifying a nucleic acid, comprising contacting the RNA molecule as claimed in claim 32 with the nucleic acid to be purified to produce a hybrid, detecting the hybrid and thereafter purifying the nucleic acid.

43. Process for sequencing a RNA molecule, comprising providing the RNA molecule as claimed in claim 32 and sequencing the RNA molecule.

* * * * *